United States Patent [19]

Hess et al.

[11] 4,238,496
[45] Dec. 9, 1980

[54] 4-SUBSTITUTED THIAZOLYL-2-OXAMIC ACIDS AND SALTS AND ESTERS THEREOF

[75] Inventors: Friedrich K. Hess, Ridgefield; Patrick B. Stewart, Washington Depot; James T. Oliver, Middlebury, all of Conn.

[73] Assignee: Boehringer Ingelheim GmbH, Ingelheim am Rhein, Fed. Rep. of Germany

[21] Appl. No.: 49,173

[22] Filed: Jun. 18, 1979

[30] Foreign Application Priority Data

Jun. 27, 1978 [DE] Fed. Rep. of Germany ....... 2828091

[51] Int. Cl.$^3$ .......................................... C07D 277/20
[52] U.S. Cl. ................... 424/270; 548/195; 544/82; 544/133; 546/275; 546/209
[58] Field of Search .............. 548/181, 195, 202; 424/270; 544/82, 133; 546/275, 209

[56] References Cited

U.S. PATENT DOCUMENTS

| 3,966,965 | 6/1976 | Sellstedt et al. .................. 424/270 |
| 4,054,666 | 10/1977 | Sellstedt et al. .................. 424/270 |

Primary Examiner—Nicholas S. Rizzo
Attorney, Agent, or Firm—Hammond & Littell

[57] ABSTRACT

Compounds of the formula

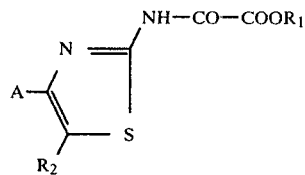

wherein
$R_1$ is hydrogen or alkyl of 1 to 4 carbon atoms;
$R_2$ is hydrogen, methyl or carboxyl; and
A is pyridyl, benzodioxanyl or

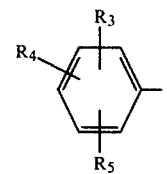

where $R_3$, $R_4$ and $R_5$, which may be identical to or different from each other, are each hydrogen, hydroxyl, alkoxy, alkyl, halogen, carboxyalkyl or nitro, or one of $R_3$, $R_4$ or $R_5$ is dialkylamino, carboxamido, morpholino, piperidino, hydroxypiperidino, cyano or phenyl;

non-toxic salts thereof formed with an inorganic base when $R_1$ is hydrogen and/or $R_2$ is carboxyl; and non-toxic addition salts thereof formed with an organic base when $R_1$ is hydrogen. The compounds are useful as antiallergics.

7 Claims, No Drawings

4-SUBSTITUTED THIAZOLYL-2-OXAMIC ACIDS AND SALTS AND ESTERS THEREOF

This invention relates to novel 4-substituted derivatives of thiazolyl-2-oxamic acid and salts and esters thereof, to methods of preparing these compounds, to pharmaceutical compositions containing them as active ingredients, and to methods of using them as antiallergics.

More particularly, the present invention relates to a novel class of thiazolyl-2-oxamic acids represented by the formula

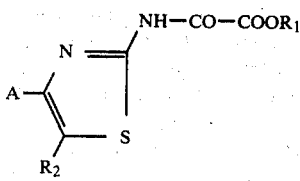

wherein
$R_1$ is hydrogen or alkyl of 1 to 4 carbon atoms;
$R_2$ is hydrogen, methyl or carboxyl; and
A is pyridyl, benzodioxanyl or

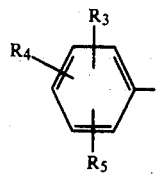

where $R_2$, $R_4$ and $R_5$, which may be identical to or different from each other, are each hydrogen, hydroxyl, alkoxy, alkyl, halogen, carboxyalkyl or nitro, or one of $R_3$, $R_4$ or $R_5$ is dialkylamino, carboxamido, morpholino, piperidino, hydroxypiperidino, cyano or phenyl;
non-toxic salts thereof formed with an inorganic base when $R_1$ is hydrogen and/or $R_2$ is carboxyl; and non-toxic addition salts therof formed with an organic base when $R_1$ is hydrogen.

The pyridyl radical included in the definition of substituent A may be 2-, 3- or 4- pyridyl.

The terms "alkyl" and "alkoxy" in the definition of $R_3$, $R_4$ and $R_5$, including the alkyl moieties of "dialkylamino" and "carboxyalkyl", refer primarily to lower alkyl and lower alkoxy, i.e. alkyl and alkoxy of 1 to 6 carbon atoms.

The term "halogen" includes fluorine, chlorine, bromine and iodine.

A preferred sub-genus is constituted by those compounds of the formula I wherein
$R_1$ is hydrogen or ethyl,
$R_2$ is hydrogen, and
A is pyridyl, benzodioxanyl or

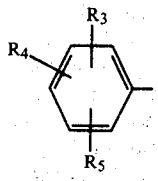

where
$R_3$ is hydrogen or hydroxyl,
$R_4$ is hydrogen, methyl or methoxy, and
$R_5$ is methyl, methoxy or dimethylamino,
and their non-toxic salts or addition salts.

Preferred species are the following:

4-(3',4'-Dimethoxy-phenyl)-thiazolyl-2-oxamic acid,
4-(4'-Dimethylamino-phenyl)-thiazolyl-2-oxamic acid,
4-Benzodioxanyl-thiazolyl-2-oxamic acid,
Ethyl 4-(2'-Pyridyl)-thiazolyl-2-oxamate,
4-(3',5'-Dimethoxy-phenyl)-thiazolyl-2-oxamic acid,
4-(3'-Hydroxy-phenyl)-thiazolyl-2-oxamic acid,
4-(4'-Hydroxy-phenyl)-thiazolyl-2-oxamic acid,
4-(3'-Methoxy-phenyl)-thiazolyl-2-oxamic acid,
Ethyl 4-(2'-hydroxy-4'-methoxy-phenyl)-thiazolyl-2-oxamate,
Ethyl 4-(4'-dimethylamino-phenyl)-thiazolyl-2-oxamate and
Ethyl 4-(2'-hydroxy-4',6'-dimethyl-phenyl)-thiazolyl-2-oxamate.

The first three compounds of the above list of species are particularly preferred.

The compounds embraced by formula I may be prepared by reacting a correspondingly substituted 2-amino-thiazole of the formula

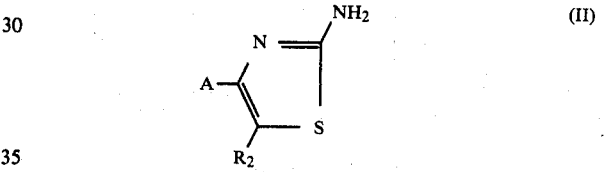

wherein A and $R_2$ have the same meanings as in formula I, with an oxalate halide, preferably the chloride, or with a dialkyl oxalate, optionally followed by hydrolysis of the ester group.

The reaction is carried out by dissolving or suspending a compound of the formula II or an acid addition salt thereof in an inert liquid medium, and admixing the oxalic acid derivative dropwise with the solution or suspension. Examples of suitable inert liquid media are benzene, toluene, xylene, lower alkanols and tetrahydrofuran. In addition, it is preferred to add an organic base, such as pyridine or triethylamine, to the reaction mixture to neutralize the acid released by the reaction. Since the reaction is strongly exothermic, the oxalic acid derivative should be added slowly and, if required, while cooling. In general, the reaction goes to completion within a time period of 30 to 180 minutes.

Since most thiazole compounds are difficultly soluble, it is of advantage to let the reaction mixture stand for an extended period of time, for instance overnight, or while stirring, before isolating the reaction product.

The reaction mixture is worked up in conventional manner, that is, by evaporating the inert liquid medium, extracting the residue with a suitable solvent or solvent mixture, such as ether, ethyl acetate, chloroform, hexane or mixtures of any two or more of these, purifying the extract solution, evaporating the solvent, and recrystallizing the residue. In some cases further purification by column chromatography has proved to be of advantage.

If it is desired to obtain an end product of the formula I wherein $R_1$ is hydrogen, the ester group is split off in conventional manner by hydrolysis, for instance by hydrolysis in the presence of a basic or acid catalyst. Suitable such catalysts are strong bases such as sodium hydroxide or potassium hydroxide, or mineral acids such as hydrochloric acid, sulfuric acid or phosphoric acid.

Those compounds of the formula I wherein $R_1$ is hydrogen and/or $R_2$ is carboxyl can, if desired, be converted into salts thereof with inorganic bases. For this purpose the free acid is dissolved or suspended in water, and the desired base is added to the solution or suspension until its pH is 7.

Likewise, those compounds wherein $R_1$ is hydrogen and/or $R_2$ is carboxyl form non-toxic addition salts with organic bases, such as ethanolamine.

Using the above indicated methods, the following end products of the formula I, optionally in the form of their salts or lower alkyl esters, can be prepared:

4-[pyridyl-(4')]-thiazolyl-2-oxamic acid,
4-[pyridyl-(3')]-thiazolyl-2-oxamic acid,
4-[pyridyl-(2')]-thiazolyl-2-oxamic acid,
4-(4'-morpholino-phenyl)-thiazolyl-2-oxamic acid,
4-(4'-methoxy-phenyl)-thiazolyl-2-oxamic acid,
4-(4'-nitro-phenyl)-thiazolyl-2-oxamic acid,
4-(4'-piperidino-phenyl)-thiazolyl-2-oxamic acid,
4-(2'-methoxy-phenyl)-thiazolyl-2-oxamic acid,
4-(2'-hydroxy-phenyl)-thiazolyl-2-oxamic acid,
4-(3',5'-dimethoxy-phenyl)-thiazolyl-2-oxamic acid,
4-(3',4'-dimethoxy-phenyl)-thiazolyl-2-oxamic acid,
4-(3'-methoxy-phenyl)-thiazolyl-2-oxamic acid,
4-(2',4'-dimethoxy-phenyl)-thiazolyl-2-oxamic acid,
4-(4'-hydroxy-phenyl)-thiazolyl-2-oxamic acid,
4-(3'-hydroxy-phenyl)-thiazolyl-2-oxamic acid,
4-(2',5'-dimethoxy-phenyl)-thiazolyl-2-oxamic acid,
4-(3',5'-dimethoxy-4'-hydroxy-phenyl)-thiazolyl-2-oxamic acid,
4-(2'-hydroxy-4'-methoxy-phenyl)-thiazolyl-2-oxamic acid,
4-(2'-hydroxy-biphenylyl)-thiazolyl-2-oxamic acid,
4-(4'-dimethylamino-phenyl)-thiazolyl-2-oxamic acid,
4-(3',4',5'-trimethoxy-phenyl)-thiazolyl-2-oxamic acid,
4-(2'-methyl-4'-hydroxy-phenyl)-thiazolyl-2-oxamic acid,
4-(benzodioxanyl)-thiazolyl-2-oxamic acid,
4-(3'-methoxy-4'-hydroxy-phenyl)-thiazolyl-2-oxamic acid,
4-(2'-methoxycarbonyl-phenyl)-thiazolyl-2-oxamic acid,
4-(4'-ethoxycarbonyl-phenyl)-thiazolyl-2-oxamic acid,
4-(4'-methoxy-phenyl)-thiazolyl-2-oxamic acid,
4-(3'-dimethylamino-phenyl)-thiazolyl-2-oxamic acid,
4-(2'-hydroxy-4',6'-dimethyl-phenyl)-thiazolyl-2-oxamic acid,
4-(3'-methyl-4'-hydroxy-phenyl)-thiazolyl-2-oxamic acid,
4-phenyl-5-methyl-thiazolyl-2-oxamic acid,
4-[pyridyl-(3)]-5-carboxy-thiazolyl-2-oxamic acid,
4-(4-fluoro-phenyl)-thiazolyl-2-oxamic acid, and
4-(4'-ethoxy-phenyl)-thiazolyl-2-oxamic acid.

The starting compounds of the formula II may be obtained, for example, by reacting thiourea with a correspondingly substituted acetophenone of the formula

A—CO—CH$_3$  (III)

wherein A has the same meaning as in formula I, according to Orteleva-King. It is of advantage to proceed according to this method described in Chemische Berichte, Volume 92, pages 35–36 (1959).

The following examples illustrate the present invention and will enable others skilled in the art to understand it more completely. It should be understood, however, that the invention is not limited solely to the particular examples given below.

EXAMPLE 1

Ethyl 4-(2'-methoxy-phenyl)-thiazolyl-2-oxamate 2.9 gm of ethyl oxalyl chloride were added dropwise to a suspension of 6 gm of 2-amino-4-(2'-methoxy-phenyl)-thiazole hydroiodide in pyridine, and the mixture was stirred overnight at room temperature. Therafter, the reaction mixture was evaporated to dryness, the residue was taken up in an aqueous sodium bicarbonate solution, and the solution was extracted several times with ether. The combined ethereal extracts were washed three times with water and once with a saturated aqueous sodium chloride solution, then dried over magnesium sulfate and finally evaporated to dryness. The residue was recrystallized from ethanol, yielding 4.2 gm (78% of theory) of the compound of the formula

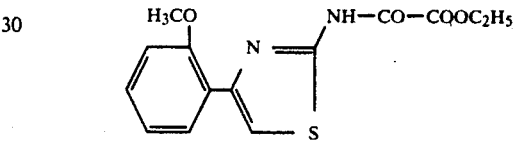

which had a melting point of 118°–120° C.

The starting compound was prepared as follows: 15 gm of o-methoxy-acetophenone was intimately admixed with 15.2 gm of thiourea in a resin flask, and 27.7 gm of iodine were added in small portions to the mixture. After all of the iodine had been added, the reaction mixture was heated overnight on an oil bath at 100°0 C. After cooling, first 50 ml of methanol and then 400 to 500 ml of water were added to the reaction mixture. The solidified mass was comminuted in a motar, the suspension was filtered, and the filter cake was washed first with water, then with some ethanol and then with ether, and finally dried. 27.7 gm (83% of theory) of 2-amino-4-(2'-methoxy-phenyl)-thiazole hydroiodide were obtained, which could be used as the starting compound without further purification.

EXAMPLE 2

Ethyl 4-(2',5'-dimethoxy-phenyl)-thiazolyl-2-oxamate

A solution of 2 gm of ethyl oxalyl chloride in 35 ml of dry pyridine was added dropwise to a solution of 3 gm of 2-amino-4-(2',5'-dimethoxy-phenyl)-thiazole in dry pyridine, and the reaction mixture was then stirred for 2½ hours at room temperature, the progress of the reaction was periodically checked by thin-layer chromatography. After the reaction had gone to completion the reaction mixture was poured into ice water, and the precipitate formed thereby was collected by filtration, washed with water and dried. After recrystallization from ethanol and n-hexane/chloroform, 2.9 gm of ethyl 4-(2',5-dimethoxy-phenyl)-thiazolyl-2-oxamate, m.p. 143°–144° C., were obtained.

EXAMPLE 3

Ethyl 4-[pyridyl-(2')]-thiazolyl-2-oxamate

A solution of 1 gm of 2-amino-4-[pyridyl-(2')]-thiazole in 25 ml of diethyl oxalate was heated for 20 hours at 125° C. Thereafter, the reaction mixture was cooled, the precipitate formed thereby was collected by filtration, and the filter cake was recrystallized first from ethanol and then from hexane/chloroform. 0.5 gm (64% of theory) of ethyl 4-[pyridyl-(2')]-thiazolyl-2-oxamate, m.p. 141°–144° C., were obtained.

EXAMPLE 4

4-(2'-Methoxy-phenyl)-thiazolyl-2-oxamic acid

A suspension of 2 gm of ethyl 4-(2-methoxy-phenyl)-thiazolyl-2-oxamate (see Example 1) in 30 ml of 1 N sodium hydroxide was heated, while vigorously stirring, until a clear solution was formed. The resulting solution was acidified with 2 N hydrochloric acid, and the precipitate formed thereby was filtered off after cooling the mixture and diluting it with water. The filter cake was suspended twice in 100 ml each of water, filtered off, and washed with ethanol, and purified by recrystallization from dimethylformamide/ethanol. 1 gm (55% of theory) of 4-(2'-methoxy-phenyl)-thiazolyl-2-oxamic acid, m.p. 195°–197° C., was obtained.

Using procedures analogous to those described in the preceding examples, the following compounds of the formula

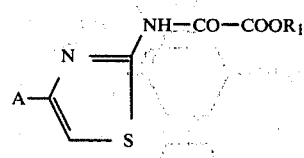

were also prepared:

| Example No. | A | $R_1$ | m.p. °C. |
|---|---|---|---|
| 5 | 3-pyridyl | $C_2H_5$ | 209–211 |
| 6 | 2-pyridyl | $C_2H_5$ | 226–228 |
| 7 | 4-morpholino-phenyl | $C_2H_5$ | 249–251 |
| 8 | 4-nitro-phenyl | $C_2H_5$ | 227–229 |
| 9 | 4-methoxy-phenyl | $C_2H_5$ | 164–165 |
| 10 | 4-piperidino-phenyl | $C_2H_5$ | 207–209 |
| 11 | 2-hydroxy-phenyl | $C_2H_5$ | 209–211 |
| 12 | 4-methoxy-phenyl (3-OCH3) | $C_2H_5$ | 166–169 |
| 13 | 3,4-dimethoxy-phenyl | H | 221–223 |
| 14 | 3,4-dimethoxy-phenyl | $C_2H_5$ | 131–133 |
| 15 | 3-methoxy-phenyl | $C_2H_5$ | 133–136 |
| 16 | 3,4-dimethoxy-phenyl (OCH3) | $C_2H_5$ | 203–207 |
| 17 | 4-hydroxy-phenyl | $C_2H_5$ | 230–233 |
| 18 | 3,4-dimethoxy-phenyl | H | >200(decomp.) |
| 19 | 3-methoxy-phenyl | H | 214–217 |
| 20 | 3,4-dimethoxy-phenyl (OCH3) | H | 190–193 |
| 21 | 3-hydroxy-phenyl | $C_2H_5$ | 231–235 |
| 22 | 3-hydroxy-phenyl · ¼ $C_2H_5OH$ | H | 211–215 |

-continued

| Example No. | A | $R_1$ | m.p. °C. |
|---|---|---|---|
| 23 | 4-HO-C₆H₄- | H | 247–250 |
| 24 | 3,4-(CH₃O)₂-5-HO-C₆H₂- | C₂H₅ | 164–168 |
| 25 | 3-CH₃O-4-HO-C₆H₃- | C₂H₅ | 167–170 |
| 26 | 3-HO-biphenyl-4-yl | C₂H₅ | 189–195 |
| 27 | 4-(CH₃)₂N-C₆H₄- | C₂H₅ | 210–213 |
| 28 | 3,4,5-(CH₃O)₃-C₆H₂- | C₂H₅ | 141–144 |
| 29 | 3-CH₃-4-HO-C₆H₃- | C₂H₅ | 173–176 |
| 30 | 3,4-(-OCH₂CH₂O-)-C₆H₃- | C₂H₅ | 204–207 |
| 31 | 4-(CH₃)₂N-C₆H₄- | H | >220(decomp.) |
| 32 | 3,4,5-(CH₃O)₃-C₆H₂- | H | 158–161 (ethanolamine salt) |
| 33 | 3-CH₃-4-HO-C₆H₃- | H | 195–197 (ethanolamine salt) |
| 34 | 3-CH₃O-4-HO-C₆H₃- | H | 177–180 (ethanolamine salt) |
| 35 | 3-HO-biphenyl-4-yl | H | >225(decomp.) |
| 36 | 2-CO₂CH₃-C₆H₄- | C₂H₅ | 139–140 |
| 37 | 3,4-(-OCH₂CH₂O-)-C₆H₃- | H | 179–181 (ethanolamine salt) |
| 38 | 2,4-(CH₃O)₂-3-OCH₃-C₆H₂- | H | 160–162 (ethanolamine salt) |
| 39 | 4-(CH₃CH₂O₂C)-C₆H₄- | C₂H₅ | 184–185 |
| 40 | 4-(CH₃CH₂O₂C)-C₆H₄- | CH₃ | 209–211 |
| 41 | 4-(CH₃CH₂O₂C)-C₆H₄- | n-Butyl | 175–177 |
| 42 | 3,5-(CH₃)₂-4-HO-C₆H₂- | CH₂H₅ | 185–187 |
| 43 | 3,4-(CH₃O)₂-C₆H₃- | CH₃ | 170–174 |
| 44 | 2-HO-C₆H₄- | H | 186–190 (ethanolamine salt) |
| 45 | 3-(CH₃)₂N-C₆H₄- | H | 147–150 (ethanolamine salt) |
| 46 | 4-O₂N-C₆H₄- | H | 230–233 (ethanolamine salt) |

-continued

| Example No. | A | R₁ | m.p. °C. |
|---|---|---|---|
| 47 | 4-hydroxy-3,5-dimethylphenyl | $C_2H_5$ | 167-170 |
| 48 | 3-hydroxy-4-methylphenyl | $C_2H_5$ | 212-215 |
| 49 | pyridyl | H | 215-219 (ethanolamine salt) |
| 50 | 4-hydroxy-3,5-dimethylphenyl | H | 207-208 (ethanolamine salt) |
| 51 | 3-hydroxy-4-methylphenyl | H | 203-207 (ethanolamine salt) |
| 52 | 4-ethoxyphenyl | $C_2H_5$ | 164-167 |
| 53 | pyridyl | H | 167-176 (ethanolamine salt) |
| 54 | 4-fluorophenyl | $C_2H_5$ | 220-223 |
| 55 | 4-ethoxyphenyl | H | 195-197 (ethanolamine salt) |
| 56 | 4-fluorophenyl | H | 197-199 (ethanolamine salt) |

In analogous manner the following compounds of the formula

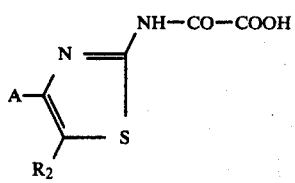

were prepared:

| Example No. | A | R₂ | m.p. °C. |
|---|---|---|---|
| 57 | pyridyl | —COOH | 204-207 (ethanolamine salt) |
| 58 | phenyl | —CH₃ | 188-190 (ethanolamine salt) |

The compounds of the present invention, that is, those embraced by formula I and their non-toxic, pharmacologically acceptable salts, have useful pharmacodynamic properties. More particularly, they exhibit very effective antiallergic activites in warm-blooded animals such as rats.

The anti-allergic properties were ascertained in rats by the Passive Cutaneous Anaphylaxis test (PCA) essentially as described by Goose and Blair (Immunology 16: 749–760,1969). Rat serum was diluted so that the skin reactions with diameters between 10 and 15 mm in unsensitized rats were produced. The PCA test was performed in duplicate by injecting 0.1 ml of this antiserum dilution on each side of the shaved back of rats. Rats so treated were injected intravenously (i.v.) twenty-four hours later with 5 mg ovalbumin in 0.5 ml of 2% Evans Blue and the test substance to be tested by the i.v. route. In the case of substances tested orally, the i.v. ovalbumin challenge was 0.015 mg in the 0.5 ml of 2% Evans Blue solution administered 20-30 minutes after the oral administration of the test substance. Thirty minutes after challenge the rats were killed by $CO_2$ asphyxiation and the skin reflected the diameters, in millimeters, of the blued areas were measured and the mean diameter determined. The circular area was calculated and the mean area in square millimeters of the control group was considered as 100% and the results of the compound test groups were expressed as a percentage change from these control values. From dose response curves the dose reducing the size of the blued area by 50% ($ED_{50}$) was estimated.

The following table shows the results of this test for a few representative specific compounds of the present invention:

| Compound | $ED_{50}$ mg/kg i.v. | $ED_{50}$ mg/kg p.o. |
|---|---|---|
| 4-(4'-dimethylamino-phenyl)-thiazolyl-2-oxamic acid | 0.02 | 0.34 |
| 4-(benzodioxanyl)-thiazolyl-2-oxamic acid ethanolamine salt | 0.02 | 0.7 |
| 4-[pyridyl-(4')]-thiazolyl-2-oxamic acid ethanolamine salt | 0.05 | — |
| 4-(3',4'-dimethoxy-phenyl)-thiazolyl-2-oxamic acid | 0.13 | — |
| 4-(3'-methoxy-phenyl)-thiazolyl-2-oxamic acid | 0.16 | 2.0 |
| 4-[pyridyl-(3')]-thiazolyl-2-oxamic acid ethanolamine salt | 0.16 | — |
| 4-phenyl-5-methyl-thiazolyl-2-oxamic acid ethanolamine salt | 0.19 | 2.04 |
| 4-(3'-dimethylamino-phenyl)-thiazolyl-2-oxamic acid ethanolamine salt | 0.34 | 1.06 |
| 4-(2',4'-dimethoxy-phenyl)-thiazolyl-2-oxamic acid | 0.39 | — |
| 4-(2',5'-dimethoxy-phenyl)-thiazolyl-2-oxamic acid ethanolamine | | |

| Compound | ED$_{50}$ mg/kg i.v. | ED$_{50}$ mg/kg p.o. |
|---|---|---|
| salt | 0.4 | — |
| 4-(2'-methoxy-phenyl)-thiazolyl-2-oxamic acid | 1.08 | |
| Ethyl 4-[pyridyl-($'$)]-thiazolyl-2-oxamate | — | 1.2 |
| Methyl 4-(3',4'-dimethoxy-phenyl)-thiazolyl-2-oxamate | — | 1.2 |
| Ethyl 4-(4'-ethoxy-phenyl)-thiazolyl-2-oxamate | — | 2.07 |
| Ethyl 4-(3'-methyl-4'-hydroxy-phenyl)-thiazolyl-2-oxamate | — | 2.1 |

The compounds of the present invention are therefore useful for the treatment of allergic asthma, hay fever, urticaria, eczema, atopic dermatitides and other allergic disorders.

For pharmaceutical purposes the compounds of the present invention are administered to warm-blooded animals perorally, parenterally, topically or by the respiratory route as active ingredients in customary dosage unit form consisting essentially of an inert pharmaceutical carrier and one effective dosage unit of the active ingredient, such as tablets, coated pills, capsules, wafers, powders, solutions, suspensions, emulsions, syrups, ointments, tinctures, aerosols and the like. One effective oral dosage unit of the compounds according to the present invention is from 0.83 to 8.3 mgm/kg body weight, and the effective parenteral or inhalation dosage unit is from 0.083 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 59

Tablets

The tablet composition is compounded from the following ingredients.

| | |
|---|---|
| 4-(3'-4'-Dimethoxy-phenyl)-thiazolyl-2-oxamic acid | 0.100 parts |
| Stearic acid | 0.010 parts |
| Dextrose | 1.890 parts |
| Total | 2.000 parts |

Preparation:

The ingredients are admixed and processed in conventional manner into 2000 mgm-tablets. Each tablet is an oral dosage unit composition containing 100 mgm of the active ingredient.

EXAMPLE 60

Ointment

The ointment composition is compounded from the following ingredients:

4-4'-Dimethylamino-phenyl)-thiazolyl-2-oxamic acid:2.000 parts.
Concentrated hydrochloric acid:0.011 parts
Sodium pyrosulfite:0.050 parts
Mixture of equal parts of cetyl alcohol and stearyl alcohol:20.000 parts
White vaseline:5.000 parts
Synthetic bergamot oil:0.075 parts
Distilled water q.s.ad:100.000 parts Preparation:

The ingredients are admixed and processed in conventional manner into an ointment, which is a topical composition containing 2.0 gm of the active ingredient per 100 gm of ointment.

EXAMPLE 61

Inhalation aerosol

The aerosol composition is compounded from the following ingredients:

4-[Benzodioxanyl-(6')]-thiazolyl-2-oxamic acid:1.00 parts
Soybean lecithin:0.20 parts
Propellant gas mixture (Frigen 11, 12 and 14) q.s.ad:100.00 parts Preparation:

The ingredients are admixed and filled in conventional manner into an aerosol container equipped with a metering valve which releases an amount of aerosol containing from 5 to 20 mgm of active ingredient with each actuation.

EXAMPLE 62

Hypodermic solution

The solution is compounded from the following ingredients:

Ethanolamine salt of 4-[pyridyl-(4')]-thiazolyl-2-oxamic acid:50.0 parts
Sodium pyrosulfite:1.0 parts
Disodium Salt of EDTA:0.5 parts
Sodium chloride:8.5 parts
Double-distilled water q.s.ad:1000.0 parts Preparation:

The ingredients are dissolved in a sufficient amount of double-distilled water, and the solution is diluted with additional double-distilled water to the desired concentration. The solution is then filtered until free from suspended particles, and the filtrate is filled under aseptic conditions in 1 cc-ampules which subsequently were sterilized and sealed. The contents of each ampule are an injectable dosage unit composition containing 50 mgm of the active ingredient.

Any one of the other compounds of the present invention may be substituted for the particular active ingredient in Examples 59 through 62. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modification may be made without departing from the spirit of the invention or the scope of the appended claims.

We claim:

1. A compound of the formula

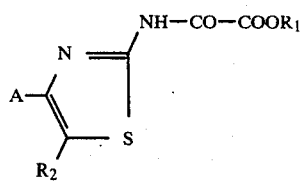

wherein
R₁ is hydrogen or alkyl of 1 to 4 carbon atoms;
R₂ is hydrogen, methyl or carboxyl; and
A is pyridyl, benzodioxanyl or

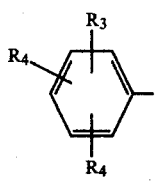

where R₃, R₄ and R₅, which may be identical to or different from each other, are each hydrogen, hydroxyl, lower alkoxy, lower alkyl, halogen, carboxy-lower alkyl or nitro, or one of R₃, R₄ or R₅ is di(lower alkyl)amino, carboxamido, morpholino, piperidino, hydroxypiperidino, cyano or phenyl;
a non-toxic salt thereof formed with an inorganic base when R₁ is hydrogen and/or R₂ is carboxyl; or a non-toxic addition salt thereof formed with an organic base when R₁ is hydrogen.

2. A compound of claim 1, where

R₁ is hydrogen or ethyl,
R₂ is hydrogen, and
A is pyridyl, benzodioxanyl or

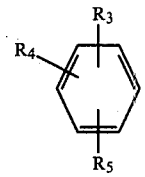

where
R₃ is hydrogen or hydroxyl,
R₄ is hydrogen, methyl or methoxy, and
R₅ is methyl, methoxy or dimethylamino.

3. A compound of claim 2, which is 4-(3',4'-dimethoxy-phenyl)-thiazolyl-2-oxamic acid or a non-toxic, pharmacologically acceptable salt thereof.

4. A compound of claim 2, which is 4-(4'-dimethylamino-phenyl)-thiazolyl-2-oxamic acid or a non-toxic pharmacologically acceptable salt thereof.

5. A compound of claim 2, which is 4-[benzodioxanyl-(6')]-thiazolyl-2-oxamic acid or a non-toxic, pharmacologically acceptable salt thereof.

6. An antiallergic pharmaceutical dosage unit composition consisting essentially of an inert pharmaceutical carrier and an effective antiallergic amount of a compound of claim 1.

7. The method of preventing or suppressing allergic reactions in warm-blooded animals in need thereof, which comprises perorally, parenterally, topically or by the respiratory route administering to said animal an effective antiallergic amount of a compound of claim 1.

* * * * *

UNITED STATES PATENT AND TRADEMARK OFFICE
CERTIFICATE OF CORRECTION

PATENT NO. : 4,238,496
DATED : December 9, 1980
INVENTOR(S) : Friedrich K. Hess et al.

It is certified that error appears in the above—identified patent and that said Letters Patent is hereby corrected as shown below:

Column 10, line 66 (table): "4-(2',4'4'-dimethoxy-"

should read -- 4-(2',4'-dimethoxy- --.

Column 11, line 7 (table): "Ethyl 4-[pyridyl-($')]"

should read: -- Ethyl 4-[pyridyl-(4')] --.

Column 11, line 63: "4-4'-Dimethylamino"

should read -- 4-(4'-Dimethylamino --.

Signed and Sealed this

Twenty-first Day of April 1981

[SEAL]

Attest:

RENE D. TEGTMEYER

*Attesting Officer*    *Acting Commissioner of Patents and Trademarks*